US012711622B2

(12) United States Patent
Fei et al.

(10) Patent No.: US 12,711,622 B2
(45) Date of Patent: Aug. 18, 2026

(54) METHOD AND SYSTEM FOR DISPLAYING X-RAY IMAGE, X- RAY MACHINE, AND STORAGE MEDIUM

(71) Applicant: Siemens Shanghai Medical Equipment Ltd., Shanghai (CN)

(72) Inventors: Xiao Ai Fei, Shanghai (CN); You Sheng Yang, Shanghai (CN)

(73) Assignee: Siemens Shanghai Medical Equipment Ltd., Shanghai (CN)

( * ) Notice: Subject to any disclaimer, the term of this patent is extended or adjusted under 35 U.S.C. 154(b) by 249 days.

(21) Appl. No.: 18/683,447

(22) PCT Filed: Sep. 18, 2021

(86) PCT No.: PCT/CN2021/119237
§ 371 (c)(1),
(2) Date: Feb. 13, 2024

(87) PCT Pub. No.: WO2023/039867
PCT Pub. Date: Mar. 23, 2023

(65) Prior Publication Data
US 2024/0354950 A1 Oct. 24, 2024

(51) Int. Cl.
*G06T 7/00* (2017.01)
*A61B 6/00* (2024.01)

(52) U.S. Cl.
CPC .............. *G06T 7/0012* (2013.01); *A61B 6/52* (2013.01); *G06T 2207/10116* (2013.01); *G06T 2207/20104* (2013.01); *G06T 2207/30168* (2013.01)

(58) Field of Classification Search
CPC . G06T 2207/10116; G06T 2207/20104; G06T 2207/30168; G06T 2207/30012; G06T 7/0012; G06T 5/92; A61B 6/52
See application file for complete search history.

(56) References Cited

U.S. PATENT DOCUMENTS 5,542,003 A 7/1996 Wofford
2008/0089602 A1* 4/2008 Heath ...................... G06T 5/94 382/274

(Continued)

FOREIGN PATENT DOCUMENTS

CN 111462115 A 7/2020
WO 2020070834 A1 4/2020

OTHER PUBLICATIONS

TORTAJADA Meritxell et al.: “Breast Peripheral Area Correction In Digital Mammograms”, vol. 50; Apr. 2, 2014; pp. 32-40; XP028848755; ISSN: 0010-4825; DOI:10.1016/J. COMPBIOMED. 2014.03.010.

(Continued)

*Primary Examiner* — Kee M Tung
*Assistant Examiner* — Thang Gia Huynh
(74) *Attorney, Agent, or Firm* — Banner & Witcoff, Ltd.

(57) ABSTRACT

Embodiments of the present disclosure disclose a method and system for displaying x-ray image, an x-ray machine, and a storage medium. The method includes: obtaining a captured current image of a target region; determining at least one to-be-optimized region in the current image; and for each to-be-optimized region, obtaining a maximum grayscale value and a minimum grayscale value in the to-be-optimized region, determining a window width and a window level for the to-be-optimized region according to the maximum grayscale value and the minimum grayscale value, and displaying the current image based on the window width and the window level. The technical solutions in the embodiments of the present disclosure can improve image display resolution of a current to-be-optimized region.

19 Claims, 4 Drawing Sheets

(56) References Cited

U.S. PATENT DOCUMENTS

| | | | |
|---|---|---|---|
| 2011/0002519 | A1 | 1/2011 | Tomisaki et al. |
| 2015/0277554 | A1 | 10/2015 | Rezaee et al. |
| 2019/0230334 | A1 | 7/2019 | Kano |
| 2021/0350513 | A1 | 11/2021 | Takahashi et al. |

OTHER PUBLICATIONS

Mar. 29, 2022 (PCT) International Search Report and Written Opinion—App PCT/CN2021/119237.

Toshimasa Hara et al: "Methods for optimizing the display conditions of brain magnetic resonance images", Japanese Journal of Radiology, Springer Japan, Tokyo, vol. 35, No. 10, Jul. 20, 2017 (Jul. 20, 2017), pp. 622-627, XP036335020, ISSN: 1867-1071, DOI: 10.1007/S11604-017-0669-0.

* cited by examiner

METHOD AND SYSTEM FOR DISPLAYING X-RAY IMAGE, X- RAY MACHINE, AND STORAGE MEDIUM

CROSS-REFERENCE TO RELATED APPLICATIONS

The present application is a U.S. National Stage entry of PCT Application no. PCT/CN2021/119237, filed Sep. 18, 2021, the contents of each of which are incorporated herein by reference in their entireties.

TECHNICAL FIELD

The present disclosure relates to the medical field and, in particular, to a method and system for displaying an X-ray image, an X-ray machine, and a non-transitory computer readable storage medium.

BACKGROUND

In an X-ray machine such as a medical C-arm machine, an X-ray source, and an X-ray receiver (such as a flat panel detector) are installed opposite to each other so that X-rays generated by the X-ray source penetrate an object and are incident on and detected by the X-ray receiver.

However, in actual application, local image overexposure caused by a large density difference of human tissue in a target region of interest is a common image quality problem. That is, an image of low-density tissue or a thin body part is overexposed, and an image of high-density tissue or a thick body part is relatively dark (i.e. underexposed). In this case, it is difficult to see all details at the same time. For example, when a chest image is scanned, the lung region is obviously overexposed.

FIG. 1 shows an X-ray image of a patient's thoracic and lumbar vertebrae. As shown in FIG. 1, an image of the thoracic vertebrae is overexposed, and an image of the lumbar vertebrae is underexposed, which makes it difficult for a doctor to clearly see the thoracic vertebrae and the lumbar vertebrae at the same time, while information of both the thoracic vertebrae and the lumbar vertebrae is usually required.

In this case, to meet different filtering requirements, currently filters of different thickness are mainly disposed between the X-ray source and the X-ray receiver to filter out different amounts of X-rays, and an ideal image requirement is achieved by switching different filters. In addition, in some applications required images are obtained by manually optimizing exposure parameters.

In addition, persons skilled in the art are still working to find other solutions.

SUMMARY

In view of this, in one aspect, embodiments of the present disclosure provide a method for displaying an X-ray image, and in another aspect, provide a system for displaying an X-ray image, an X-ray machine, and a computer readable storage medium, so as to improve image display resolution of a current to-be-optimized region.

An embodiment of the present disclosure proposes a method for displaying an X-ray image, including: obtaining a captured current image of a target region; determining at least one to-be-optimized region in the current image; and for each to-be-optimized region, obtaining a maximum grayscale value and a minimum grayscale value in the to-be-optimized region, determining a window width and a window level for the to-be-optimized region according to the maximum grayscale value and the minimum grayscale value, and displaying the current image based on the window width and the window level.

In an implementation, the determining at least one to-be-optimized region in the current image includes: detecting whether a to-be-optimized region exists in the current image, and determining each detected to-be-optimized region as a to-be-optimized region in the current image.

In an implementation, the detecting whether a to-be-optimized region exists in the current image, and determining each detected to-be-optimized region as a to-be-optimized region in the current image includes: detecting a pixel whose brightness value is greater than a preset first brightness threshold in the current image, to obtain an overexposed pixel; and when a quantity of overexposed pixels reaches a preset first quantity threshold, determining that a to-be-optimized overexposed bright region exists in the current image, determining a to-be-optimized region corresponding to the bright region based on distribution of the overexposed pixels, and determining the to-be-optimized region as a to-be-optimized region in the current image; and/or detecting a pixel whose brightness value is less than a preset second brightness threshold in the current image, to obtain an over-dark pixel; and when a quantity of over-dark pixels reaches a preset second quantity threshold, determining that a to-be-optimized underexposed dark region exists in the current image, determining a to-be-optimized region corresponding to the dark region based on distribution of the over-dark pixels, and determining the to-be-optimized region as a to-be-optimized region in the current image.

In an implementation, the determining at least one to-be-optimized region in the current image includes: obtaining at least one to-be-optimized region manually selected by a user from the current image, and determining the at least one to-be-optimized region as at least one to-be-optimized region in the current image.

In an implementation, the determining a window width and a window level for the to-be-optimized region according to the maximum grayscale value and the minimum grayscale value includes: using a difference between the maximum grayscale value and the minimum grayscale value as the window width for the to-be-optimized region; and using an average value of the maximum grayscale value and the minimum grayscale value or an average value of all pixels in the to-be-optimized region as the window level for the to-be-optimized region.

An embodiment of the present disclosure proposes a system for displaying an X-ray image, including: a first unit, configured to obtain a captured current image of a target region; a second unit, configured to determine at least one to-be-optimized region in the current image; and a third unit, configured to: for each to-be-optimized region, obtain a maximum grayscale value and a minimum grayscale value in the to-be-optimized region, determine a window width and a window level for the to-be-optimized region according to the maximum grayscale value and the minimum grayscale value, and display the current image based on the window width and the window level.

In an implementation, the second unit detects whether a to-be-optimized region exists in the current image, and determines each detected to-be-optimized region as a to-be-optimized region in the current image In an implementation, the second unit detects a pixel whose brightness value is greater than a preset first brightness threshold in the current image, to obtain an overexposed pixel; and when a quantity of overexposed pixels reaches a preset first quantity threshold, determines that a to-be-optimized overexposed bright region exists in the current image, and determines a to-be-optimized region corresponding to the bright region based on distribution of the overexposed pixels; and/or detects a pixel whose brightness value is less than a preset second brightness threshold in the current image, to obtain an over-dark pixel; and when a quantity of over-dark pixels reaches a preset second quantity threshold, determines that a to-be-optimized underexposed dark region exists in the current image, and determines a to-be-optimized region corresponding to the dark region based on distribution of the over-dark pixels.

In an implementation, the second unit obtains at least one to-be-optimized region manually selected by a user from the current image, and determines the at least one to-be-optimized region as at least one to-be-optimized region in the current image.

In an implementation, the third unit includes: an obtaining module, configured to: for each to-be-optimized region, obtain a maximum grayscale value and a minimum grayscale value in the to-be-optimized region; a determining module, configured to use a difference between the maximum grayscale value and the minimum grayscale value that are obtained by the obtaining module as the window width for the to-be-optimized region; and use an average value of the maximum grayscale value and the minimum grayscale value or an average value of all pixels in the to-be-optimized region as the window level for the to-be-optimized region; and a display module, configured to display the current image based on the window width and the window level determined by the determining module.

An embodiment of the present disclosure proposes another system for displaying an X-ray image, including at least one memory and at least one processor, where: the at least one memory is configured to store a computer program; and the at least one processor is configured to invoke the computer program stored in the at least one memory to perform the method for displaying an X-ray image in any implementation above.

An embodiment of the present disclosure proposes an X-ray machine, including the system for displaying an X-ray image in any implementation above.

An embodiment of the present disclosure proposes a computer readable storage medium on which a computer program is stored, where the computer program can be executed by a processor to implement the method for displaying an X-ray image in any implementation above.

It can be learned from the foregoing solutions that, in the embodiments of the present disclosure, a window width and a window level for clearly displaying a to-be-optimized region can be automatically calculated according to a maximum grayscale value and a minimum grayscale value in the over-bright and/or over-dark to-be-optimized region in a current image, and then the current image is displayed based on the window width and the window level, so that each to-be-optimized region in the current image can be clearly displayed without requiring manual adjustment by a user.

In addition, the over-bright and/or over-dark to-be-optimized region can be automatically detected by a system, thereby further improving system intelligence and operation convenience.

BRIEF DESCRIPTION OF THE DRAWINGS

To enable a person of ordinary skill in the art to understand the foregoing and other features and advantages of the present disclosure more clearly, embodiments according to the present disclosure are described in detail below with reference to the accompany drawings. In the accompany drawings.

Figure 1:
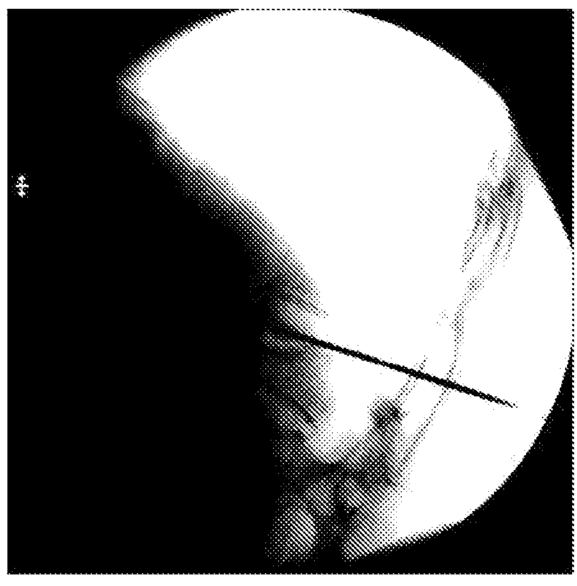
FIG. 1 illustrates an example X-ray image of a patient's thoracic and lumbar vertebrae.

Reference numerals are as follows:

| Reference sign | Meaning |
|---|---|
| S21-S23 | Blocks |
| 31 | To-be-optimized region on a thoracic vertebrae side |
| 32 | To-be-optimized region on a lumbar vertebrae side |
| 410 | First unit |
| 420 | Second unit |
| 430 | Third unit |
| 431 | Obtaining module |
| 432 | Determining module |
| 433 | Display module |
| 51 | Memory |
| 52 | Processor |
| 53 | Display |
| 54 | Bus |

DETAILED DESCRIPTION OF THE DISCLOSURE

In embodiments of the present disclosure, a captured X-ray image actually includes all image information. When the image is displayed, to meet display requirements of both a bright region and a dark region, a display tradeoff is made. Consequently, neither an overexposed bright region nor an underexposed dark region is in an optimal display condition. Therefore, in the embodiments, to avoid an excessively complex operation on an image collection side, image display resolution is optimized from a perspective of image display.

Therefore, in the embodiments of the present disclosure, a window technology is considered to improve image display resolution of a current to-be-optimized region. The window technology is a display technology used in X-ray examination to observe normal tissue or lesions of different density, and includes a window width and a window level. Because various normal or lesion tissue structures have different grayscale values, when details of a certain tissue structure are to be displayed, a window width and a window level suitable for observing the tissue structure need to be selected for optimal display. The window width is a grayscale value range displayed on an X-ray image. Tissue structures in the grayscale value range are displayed using different simulated grayscales. A tissue structure whose grayscale value is higher than values in the range is displayed in a white shadow, and no grayscale difference exists. On the contrary, a tissue structure whose grayscale value is lower than the values in the range is displayed in a dark shadow, and no grayscale difference exists If the window width is increased, the grayscale value range shown in the image is increased, and more tissue structures with different density are displayed, but a grayscale difference between the structures is reduced. When the window width is decreased, fewer tissue structures are displayed, but a grayscale difference between the structures is increased. The window level is a center position of a window, and grayscale values of a grayscale value range included in the same window width are also different when window levels are different.

At present, to observe different tissue structures, users need to select different window widths and window levels based on experience. However, in the implementation that users choose different window widths and window levels based on their experience for different tissue structures, on one hand high requirements are imposed on user experience, and on the other hand it is not convenient to perform operations, and multiple tests may be required to find satisfactory window widths and window levels.

In view of this, in the embodiments of the present disclosure, a window width and a window level for clearly displaying a to-be-optimized region in a current image can be automatically selected by a system based on the to-be-optimized region.

To make the objectives, technical solutions, and advantages of the present disclosure clearer, the present disclosure is further described in detail below with reference to the embodiments.

Figure 2:
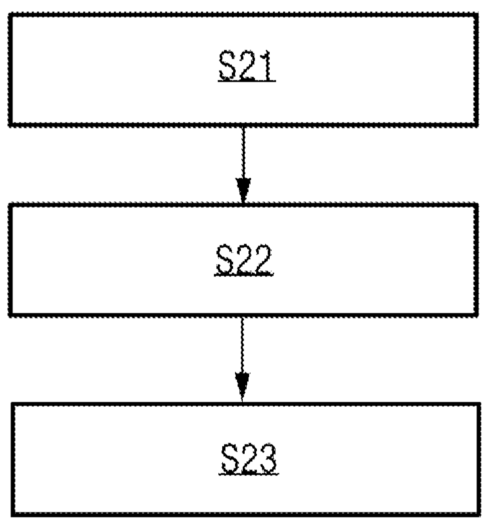
FIG. 2 illustrates an example flowchart of a method for displaying an X-ray image according to an embodiment of the present disclosure.

FIG. 2 is an example flowchart of a method for displaying an X-ray image according to an embodiment of the present disclosure. As shown in FIG. 2, the method may include the following:

Block S21: Obtain a captured current image of a target region.

In this block, the target region may be a to-be-imaged region required by a user in a clinical operation, and the target region may change according to an actual application. When the target region changes, the image obtained in block S21 also correspondingly changes.

In specific implementation, after an organ program is determined, the solution in this embodiment may be executed in real time, and correspondingly, block S21 is also performed in real time. Alternatively, the solution may be periodically performed, and correspondingly, block S21 is also periodically performed. Alternatively, the solution may be triggered by a condition, and correspondingly, block S21 may be triggered when the target region is initially determined and when the target region changes.

Block S22: Determine at least one to-be-optimized region in the current image.

In this embodiment, the user may manually select at least one to-be-optimized region from the current image. For example, the user selects a to-be-optimized region corresponding to a bright region on a bright thoracic vertebrae side in FIG. 1, and for another example, selects a to-be-optimized region corresponding to a dark region on a dark lumbar vertebrae side in FIG. 1. Accordingly, a system may determine the at least one to-be-optimized region selected by the user as at least one to-be-optimized region in the current image. Further, the to-be-optimized region may be further identified in the current image. In this case, the bright region refers to a region that is determined as a bright region based on experience of the user, and the dark region is a region that is determined as a dark region based on experience of the user.

Alternatively, in this embodiment the system may automatically determine the to-be-optimized region in the current image. Correspondingly, in this embodiment, whether a to-be-optimized region exists in the current image may be detected, and each detected to-be-optimized region is determined as a to-be-optimized region in the current image. The to-be-optimized region includes an overexposed bright region and/or an underexposed dark region. For example, in specific implementation, a pixel whose brightness value is greater than a preset first brightness threshold in the current image may be detected based on a histogram technology, to obtain an overexposed pixel; and when a quantity of overexposed pixels reaches a preset first quantity threshold, it is determined that a to-be-optimized overexposed bright region exists in the current image, and a to-be-optimized region corresponding to the bright region may be determined based on distribution of the overexposed pixels; otherwise, it may be determined that no to-be-optimized overexposed bright region exists in the current image; and/or a pixel whose brightness value is less than a preset second brightness threshold in the current image is detected based on the histogram technology, to obtain an over-dark pixel; and when a quantity of over-dark pixels reaches a preset second quantity threshold, it is determined that a to-be-optimized underexposed dark region exists in the current image, and a to-be-optimized region corresponding to the dark region may be determined based on distribution of the over-dark pixels; otherwise, it may be determined that no to-be-optimized underexposed dark region exists in the current image. The second brightness threshold is less than or equal to the first brightness threshold. In specific implementation, for example, grayscale gradient distribution of the bright region and/or the dark region may be determined by using an image gradient calculation algorithm, so as to detect an edge of the bright region and/or the dark region, and then a bright region boundary and/or a dark region boundary are fitted by using an edge curve. In this case, the bright region may be a region in which the quantity of pixels whose brightness is greater than the preset first brightness threshold reaches the first quantity threshold, and the dark region may be a region in which the quantity of pixels whose brightness is less than the preset second brightness threshold reaches the second quantity threshold.

In addition, in other embodiments, the bright region may also refer to a region in which an exposure degree is higher than a first exposure degree, and the dark region may also refer to a region in which the exposure degree is lower than a second exposure degree. The second exposure degree is less than the first exposure degree.

Block S23: For each to-be-optimized region, obtain a maximum grayscale value and a minimum grayscale value in the to-be-optimized region, determine a window width and a window level for the to-be-optimized region according to the maximum grayscale value and the minimum grayscale value, and display the current image based on the window width and the window level.

The maximum grayscale value and the minimum grayscale value in this block may be a maximum grayscale value and a minimum grayscale value that are in all pixels of the to-be-optimized region, or may be a maximum pixel value and a minimum pixel value that are in a specific pixel interval of the to-be-optimized region.

In addition, there may be multiple methods for determining the window width and the window level for the to-be-optimized region according to the maximum grayscale value and the minimum grayscale value. For example, assuming that a minimum grayscale value in a certain to-be-optimized region is A and a maximum grayscale value is B, the window width (WW) may be B-A, and the window level (WL) may be (A+B)/2. Alternatively, the window level (WL) may be an average value of all pixels in the to-be-optimized region. In addition, in another implementation, the window width and the window level may also be calculated by using another calculation method, which is not limited herein.

Figure 3A:
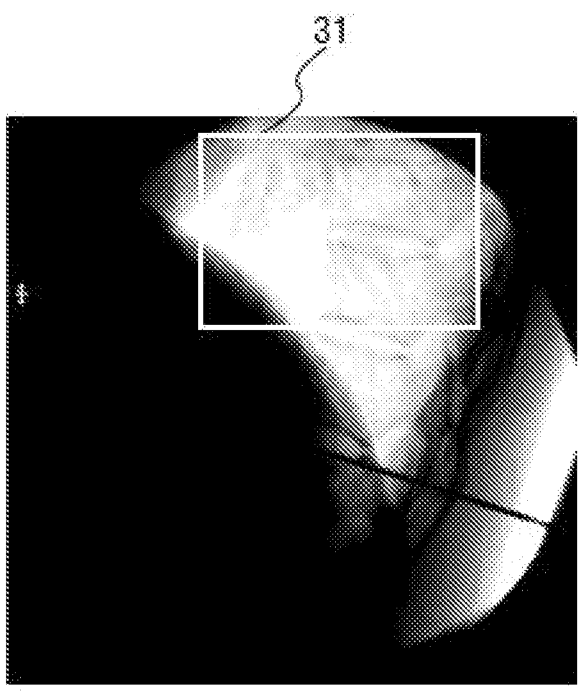
FIG. 3A illustrates an example display image obtained after a window width and a window level are adjusted for a to-be-optimized region on a thoracic vertebrae side shown in a frame 31 of the X-ray image shown in FIG. 1 according to an embodiment of the present disclosure.
Figure 3B:
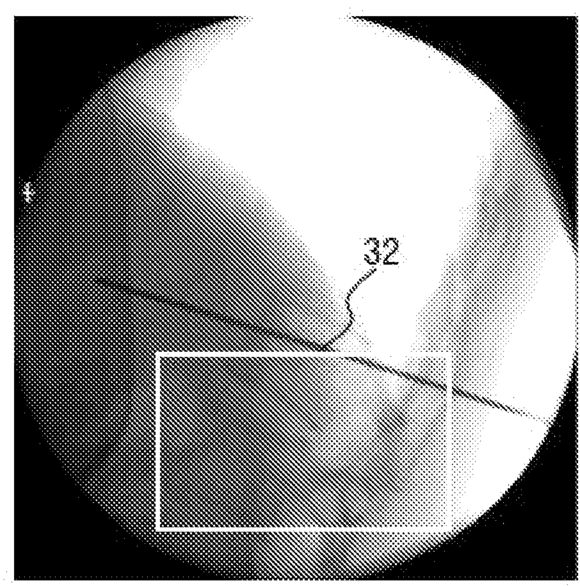
FIG. 3B illustrates an example display image obtained after a window width and a window level are adjusted for a to-be-optimized region on a lumbar vertebrae side shown in a frame 32 of the X-ray image shown in FIG. 1 according to an embodiment of the present disclosure.

FIG. 3A is a display image obtained after a window width and a window level are adjusted for a to-be-optimized region on a thoracic vertebrae side shown in a frame 31 of the X-ray image shown in FIG. 1. FIG. 3B is a display image obtained after a window width and a window level are adjusted for a to-be-optimized region on a lumbar vertebrae side shown in a frame 32 of the X-ray image shown in FIG. 1. It may be learned that a display image obtained after a window width and a window level are automatically adjusted for a specific to-be-optimized region can clearly display the to-be-optimized region.

The foregoing describes in detail a method for displaying an X-ray image in the embodiments of the present disclosure, and the following further describes in detail a system for displaying an X-ray image in the embodiments of the present disclosure. The system for displaying an X-ray image in the embodiments of the present disclosure may be configured to implement the method for displaying an X-ray image in the embodiments of the present disclosure. For details not disclosed in the system embodiments of the present disclosure, refer to corresponding descriptions in the method embodiments of the present disclosure. Details are not described herein again.

Figure 4:
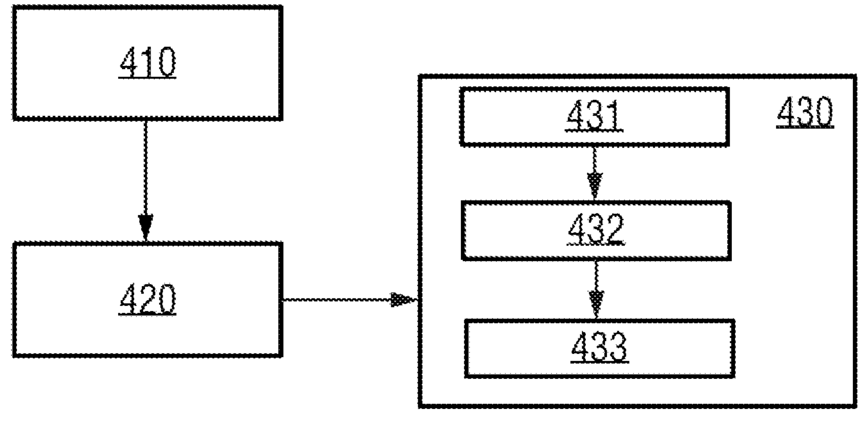
FIG. 4 illustrates an example structural diagram of a system for displaying an X-ray image according to an embodiment of the present disclosure.

FIG. 4 is an example structural diagram of a system for displaying an X-ray image according to an embodiment of the present disclosure. As shown in FIG. 4, the system includes a first unit 410, a second unit 420, and a third unit 430, which may alternatively be referred to herein as processing circuitry or processors.

The first unit 410 is configured to obtain a captured current image of a target region.

The second unit 420 is configured to determine at least one to-be-optimized region in the current image. In specific implementation, the second unit 420 may obtain at least one to-be-optimized region manually selected by a user from the current image, and determine the at least one to-be-optimized region as at least one to-be-optimized region in the current image. Alternatively, the second unit 420 may detect whether a to-be-optimized region exists in the current image, and determine each detected to-be-optimized region as a to-be-optimized region in the current image For example, the second unit 420 detects a pixel whose brightness value is greater than a preset first brightness threshold in the current image based on a histogram technology, to obtain an overexposed pixel; and when a quantity of overexposed pixels reaches a preset first quantity threshold, determine that a to-be-optimized overexposed bright region exists in the current image, and determine a to-be-optimized region corresponding to the bright region based on distribution of the overexposed pixels; otherwise, may determine that no to-be-optimized overexposed bright region exists in the current image; and/or detects a pixel whose brightness value is less than a preset second brightness threshold in the current image, to obtain an over-dark pixel; and when a quantity of over-dark pixels reaches a preset second quantity threshold, determines that a to-be-optimized underexposed dark region exists in the current image, and determines a to-be-optimized region corresponding to the dark region based on distribution of the over-dark pixels; otherwise, may determine that no to-be-optimized underexposed dark region exists in the current image. In specific implementation, for example, grayscale gradient distribution of the bright region and/or the dark region may be determined by using an image gradient calculation algorithm, so as to detect an edge of the bright region and/or the dark region, and then a bright region boundary and/or a dark region boundary are fitted by using an edge curve.

The third unit 430 is configured to: for each to-be-optimized region, obtain a maximum grayscale value and a minimum grayscale value in the to-be-optimized region, determine a window width and a window level for the to-be-optimized region according to the maximum grayscale value and the minimum grayscale value, and display the current image based on the window width and the window level. The maximum grayscale value and the minimum grayscale value may be a maximum grayscale value and a minimum grayscale value that are in all pixels of the to-be-optimized region, or may be a maximum pixel value and a minimum pixel value that are in a specific pixel interval of the to-be-optimized region.

In specific implementation, the third unit 430 may include an obtaining module 431 (also referred to herein as obtaining processing circuitry, an obtaining processor, or an obtainer), a determining module 432 (also referred to herein as determining processing circuitry, a determining processor, or an determiner), and a display module 433 (also referred to herein as a display).

The obtaining module 431 is configured to: for each to-be-optimized region, obtain a maximum grayscale value and a minimum grayscale value in the to-be-optimized region.

The determining module 432 is configured to determine a window width and a window level for the to-be-optimized region according to the maximum grayscale value and the minimum grayscale value that are obtained by the obtaining module 431; for example, may use a difference between the maximum grayscale value and the minimum grayscale value as the window width for the to-be-optimized region; and use an average value of the maximum grayscale value and the minimum grayscale value or an average value of all pixels in the to-be-optimized region as the window level for the to-be-optimized region. Alternatively, the determining module 432 may determine the window width and the window level by using another calculation method.

The display module 433 is configured to display the current image based on the window width and the window level determined by the determining module 432.

Figure 5:
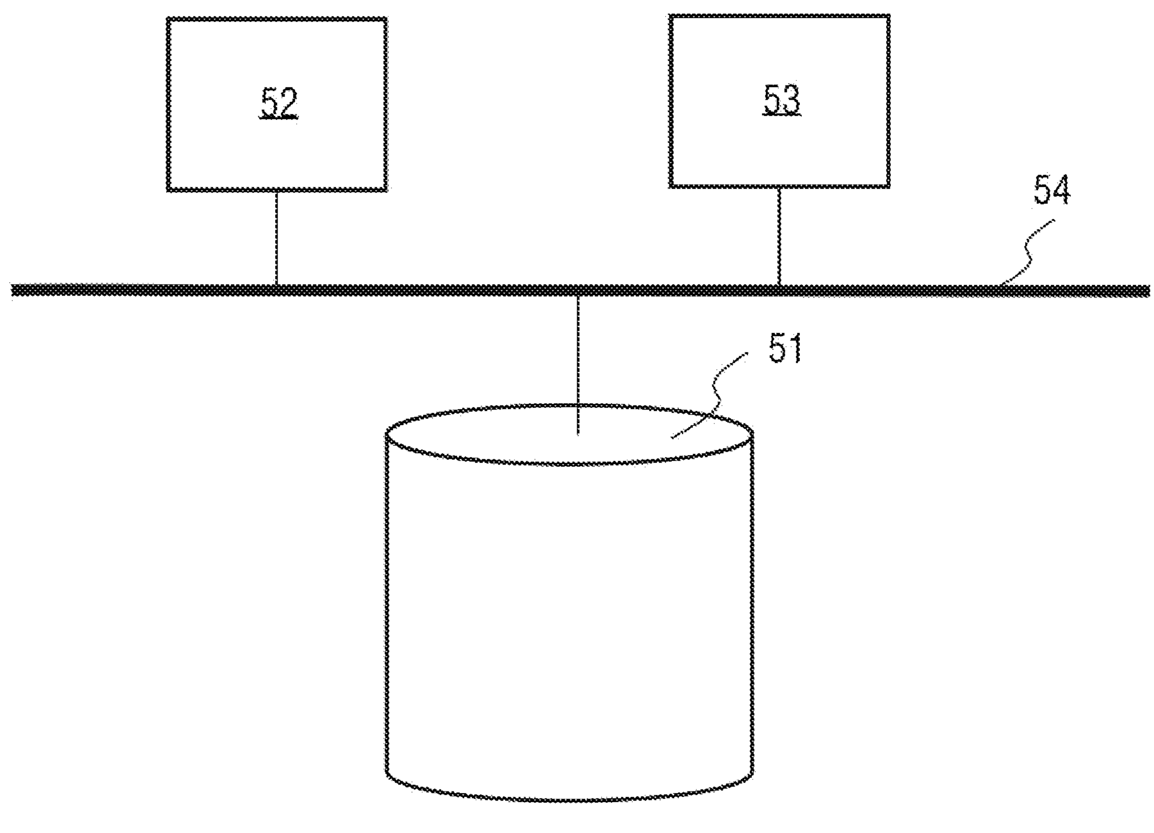
FIG. 5 illustrates an example structural diagram of another system for displaying an X-ray image according to an embodiment of the present disclosure.

FIG. 5 is a schematic structural diagram of another system for displaying an X-ray image according to an embodiment of the present disclosure. As shown in FIG. 5, the system may include at least one memory 51 (e.g. a non-transitory computer-readable medium), at least one processor 52, and at least one display 53. In addition, some other components, such as a communications port, may be further included. These components communicate with each other by using a bus 54.

The at least one memory 51 is configured to store a computer program. In an implementation, the computer program may be understood as including each module in the system for displaying an X-ray image shown in FIG. 4. In addition, the at least one memory 51 may further store an operating system and the like. The operating system includes but is not limited to an Android operating system, a Symbian operating system, a Windows operating system, a Linux operating system, and the like.

The at least one display 53 is configured to display a captured current image, man-machine interaction information, display the current image based on an adjusted window width and window level, and the like.

The at least one processor 52 is configured to invoke the computer program stored in the at least one memory 51 to perform the method for displaying an X-ray image in the embodiments of the present disclosure. The processor 52 may be a CPU, a processing unit/module, an ASIC, a logic module, a programmable gate array, or the like. It may receive and send data by using the communications port.

An embodiment of the present disclosure further provides an X-ray machine, including the system for displaying an X-ray image in any one of the foregoing implementations.

It should be noted that not all blocks, units, and modules in the procedures and the structural diagrams are necessary, and some blocks, units, or modules may be omitted according to an actual need. An execution sequence of the blocks is not fixed and may be adjusted according to needs. Division of the units and modules is merely functional division for ease of description. During actual implementation, one unit and/or module may be implemented separately by a plurality of units and/or modules, respectively, and functions of the plurality of units and/or modules may alternatively be implemented by the same unit and/or module, as the case may be. The units and/or modules may be located in the same device or in different devices.

It may be understood that hardware units and/or modules in the foregoing implementations may be implemented in a mechanical manner or an electronic manner. For example, one hardware unit and/or module may include a specially designed permanent circuit or logic device (such as a dedicated processor, such as an FPGA or an ASIC) configured to complete a particular operation. The hardware unit and/or module may alternatively include a programmable logical device or circuit (for example, including a general processor or another programmable processor) configured temporarily by software and configured to perform a specific operation. Whether the hardware unit and/or module is specifically implemented in the mechanical manner, by using the dedicated permanent circuit, or by using the provisionally configured circuit (such as a circuit configured by software) may be decided in consideration of costs and time.

In addition, an embodiment of the present disclosure further provides a computer-readable storage medium, storing a computer program, the computer program, when executed by a processor, implementing the method for displaying the X-ray image in the embodiments of the present disclosure. Specifically, a system or an apparatus provided with a storage medium may be provided. The storage medium stores software program code for implementing the functions of any one of the foregoing implementations, and a computer (or a CPU or MPU) of the system or the apparatus is enabled to read and execute program code stored in the storage medium. In addition, an operating system and the like operated on a computer are enabled to some or all of actual operations by using instructions based on the program code. The program code read from the storage medium may be written into a memory inserted into an expansion board inserted in the computer or a memory written to an expansion unit connected to the computer, and then the instructions based on the program enable a CPU or the like installed on the expansion board or the expansion unit to perform some and all actual operations, thereby implementing the functions of any one of the foregoing implementations. Implementations for providing the storage medium of the program code include a floppy disk, a hard disk, a magneto-optical disk, an optical disc (for example, a CD-ROM, a CD-R, a CD-RW, a DVD-ROM, a DVD-RAM, a DVD-RW, or a DVD+RW), a magnetic tape, a non-volatile storage card, and a ROM. Optionally, the program code may be downloaded from a server computer by using a communication network.

It can be learned from the foregoing solutions that, in the embodiments of the present disclosure, a window width and a window level for clearly displaying a to-be-optimized region can be automatically calculated according to a maximum grayscale value and a minimum grayscale value in the over-bright and/or over-dark to-be-optimized region in a current image, and then the current image is displayed based on the window width and the window level, so that each to-be-optimized region in the current image can be clearly displayed without requiring manual adjustment by a user.

In addition, the over-bright and/or over-dark to-be-optimized region can be automatically detected by a system, thereby further improving system intelligence and operation convenience.

The foregoing descriptions are exemplary embodiments of the present disclosure, but are not intended to limit the present disclosure. Any modification, equivalent replacement, or improvement made within the spirit and principle of the present disclosure shall fall within the protection scope of the present disclosure.

The various components described herein may be referred to as "units," "modules," or "systems." Such components may be implemented via any suitable combination of hardware and/or software components as applicable and/or known to achieve their intended respective functionality. This may include mechanical and/or electrical components, processors, processing circuitry, or other suitable hardware components, in addition to or instead of those discussed herein. Such components may be configured to operate independently, or configured to execute instructions or computer programs that are stored on a suitable computer-readable medium. Regardless of the particular implementation, such units, modules, and/or systems, as applicable and relevant, may alternatively be referred to herein as "circuitry," "controllers," "processors," or "processing circuitry," or alternatively as noted herein.

What is claimed is:

1. A method for displaying an X-ray image, comprising:
obtaining a captured current image of a target region;
determining at least one to-be-optimized region in the current image, comprising:
detecting whether a to-be-optimized region exists in the current image by detecting a pixel having a brightness value less than a preset brightness threshold in the current image to obtain an underexposed pixel and, when a quantity of underexposed pixels reaches a preset quantity threshold, (i) determining that a to-be-optimized underexposed dark region exists in the current image, and (ii) determining a to-be-optimized region corresponding to the underexposed dark region based on a distribution of the underexposed pixels, and
determining each detected to-be-optimized region as a to-be-optimized region in the current image; and
for each to-be-optimized region:
obtaining a maximum grayscale value and a minimum grayscale value in the to-be-optimized region;

determining a window width and a window level for the to-be-optimized region according to the maximum grayscale value and the minimum grayscale value by:

using a difference between the maximum grayscale value and the minimum grayscale value as the window width for the to-be-optimized region; and using (i) an average value of the maximum grayscale value and the minimum grayscale value, or (ii) an average value of all pixels in the to-be-optimized region, as the window level for the to-be-optimized region; and displaying the current image based on the window width and the window level.

2. The method according to claim 1, wherein the detecting whether a to-be-optimized region exists in the current image and determining each detected to-be-optimized region as a to-be-optimized region in the current image further comprises:

detecting a pixel having a brightness value greater than a preset further brightness threshold in the current image to obtain an overexposed pixel;

when a quantity of overexposed pixels reaches a preset further quantity threshold:

determining that a to-be-optimized overexposed bright region exists in the current image;

determining a to-be-optimized region corresponding to the overexposed bright region based on a distribution of the overexposed pixels.

3. The method according to claim 2, wherein the preset brightness threshold is less than or equal to the preset further brightness threshold.

4. The method according to claim 1, wherein the determining the at least one to-be-optimized region in the current image comprises obtaining at least one to-be-optimized region that has been manually selected by a user from the current image.

5. The method according to claim 1, wherein detecting whether a to-be-optimized region exists in the current image is performed based on a histogram.

6. The method according to claim 1, wherein determining the to-be-optimized region corresponding to the underexposed dark region comprises using an image gradient calculation algorithm to detect an edge of the underexposed dark region and fitting a boundary of the underexposed dark region using an edge curve.

7. A system for displaying an X-ray image, comprising:

first processing circuitry configured to obtain a captured current image of a target region;

second processing circuitry configured to determine at least one to-be-optimized region in the current image by:

detecting whether a to-be-optimized region exists in the current image by detecting a pixel having a brightness value less than a preset brightness threshold in the current image to obtain an underexposed pixel, and, when a quantity of underexposed pixels reaches a preset quantity threshold, (i) determining that a to-be-optimized underexposed dark region exists in the current image, and (in) determining a to-be-optimized region corresponding to the underexposed dark region based on a distribution of the underexposed pixels; and determining each detected to-be-optimized region as a to-be-optimized region in the current image; and third processing circuitry configured to, for each to-be-optimized region:

obtain a maximum grayscale value and a minimum grayscale value in the to-be-optimized region;

determine a window width and a window level for the to-be-optimized region according to the maximum grayscale value and the minimum grayscale value by:

using a difference between the maximum grayscale value and the minimum grayscale value as the window width for the to-be-optimized region; and using (i) an average value of the maximum grayscale value and the minimum grayscale value, or (ii) an average value of all pixels in the to-be-optimized region, as the window level for the to-be-optimized region; and display the current image based on the window width and the window level.

8. The system according to claim 7, wherein the second processing circuitry is further configured to:

detect a pixel having a brightness value greater than a preset further brightness threshold in the current image to obtain an overexposed pixel;

when a quantity of overexposed pixels reaches a preset first-further quantity threshold:

determine that a to-be-optimized overexposed bright region exists in the current image; and determine a to-be-optimized region corresponding to the overexposed bright region based on a distribution of the overexposed pixels.

9. The system according to claim 8, wherein the preset brightness threshold is less than or equal to the preset further brightness threshold.

10. The system according to claim 7, wherein the second processing circuitry is configured to:

obtain at least one to-be-optimized region that is manually selected by a user from the current image; and determine the at least one to-be-optimized region as at least one to-be-optimized region in the current image.

11. The system according to claim 7, wherein the system is part of an X-ray machine.

12. The system according to claim 7, wherein the second processing circuitry is configured to detect whether a to-be-optimized region exists in the current image based on a histogram.

13. The system according to claim 7, wherein the second processing circuitry is configured to determine the to-be-optimized region corresponding to the underexposed dark region by using an image gradient calculation algorithm to detect an edge of the underexposed dark region and fitting a boundary of the underexposed dark region using an edge curve.

14. A non-transitory computer-readable storage medium on which a computer program is stored that, when executed by a processor, cause an X-ray image to be displayed by:

obtaining a captured current image of a target region;

determining at least one to-be-optimized region in the current image by:

detecting whether a to-be-optimized region exists in the current image by detecting a pixel having a brightness value less than a preset brightness threshold in the current image to obtain an underexposed pixel, and, when a quantity of underexposed pixels reaches a preset quantity threshold, determining that a to-be-optimized underexposed dark region exists in the current image, and determining a to-be-optimized region corresponding to the underexposed dark region based on a distribution of the underexposed pixels; and determining each detected to-be-optimized region as a to-be-optimized region in the current image; and for each to-be-optimized region:

obtaining a maximum grayscale value and a minimum grayscale value in the to-be-optimized region;

determining a window width and a window level for the to-be-optimized region according to the maximum grayscale value and the minimum grayscale value by:

using a difference between the maximum grayscale value and the minimum grayscale value as the window width for the to-be-optimized region; and using (i) an average value of the maximum grayscale value and the minimum grayscale value, or (ii) an average value of all pixels in the to-be-optimized region, as the window level for the to-be-optimized region; and displaying the current image based on the window width and the window level.

15. The non-transitory computer-readable storage medium according to claim 14, wherein the computer program, when executed by a processor, further causes the detection of whether the to-be-optimized region exists in the current image and the determination of each detected to-be-optimized region as a to-be-optimized region in the current image by:

detecting a pixel having a brightness value greater than a preset further brightness threshold in the current image to obtain an overexposed pixel; and when a quantity of overexposed pixels reaches a preset further quantity threshold:

determining that a to-be-optimized overexposed bright region exists in the current image; and determining a to-be-optimized region corresponding to the overexposed bright region based on a distribution of the overexposed pixels.

16. The non-transitory computer-readable storage medium according to claim 15, wherein the preset brightness threshold is less than or equal to the preset further brightness threshold.

17. The non-transitory computer-readable storage medium according to claim 14, wherein the computer program, when executed by a processor, further causes the at least one to-be-optimized region in the current image to be determined by obtaining at least one to-be-optimized region that has been manually selected by a user from the current image.

18. The non-transitory computer-readable storage medium according to claim 14, wherein the computer program, when executed by a processor, further causes the detection of whether a to-be-optimized region exists in the current image based on a histogram.

19. The non-transitory computer-readable storage medium according to claim 14, wherein the computer program, when executed by a processor, further causes the determination of a to-be-optimized region corresponding to the underexposed dark region by using an image gradient calculation algorithm to detect an edge of the underexposed dark region and fitting a boundary of the underexposed dark region using an edge curve.

* * * * *